United States Patent [19]

Lackler et al.

[11] Patent Number: 4,844,409
[45] Date of Patent: Jul. 4, 1989

[54] MEDICAL GAS ADAPTER WITH MOLDED SPRING BIAS

[75] Inventors: Peter A. Lackler, Silver Spring, Md.; Douglas D. Carden, Barneveld, Wis.

[73] Assignee: The BOC Group, Inc., Montvale, N.J.

[21] Appl. No.: 261,794

[22] Filed: Oct. 24, 1988

[51] Int. Cl.$^4$ ............................................. F16L 29/00
[52] U.S. Cl. .................................. 251/149.9; 285/308
[58] Field of Search ................... 251/148, 149.6, 149.9; 137/614.05, 614.21, 329.1; 285/305, 307, 308

[56] References Cited

U.S. PATENT DOCUMENTS

| | | | |
|---|---|---|---|
| 2,905,487 | 9/1959 | Sclufter | 137/630.22 |
| 3,563,267 | 2/1971 | Thompson | 137/614.21 X |

Primary Examiner—A. Michael Chambers
Assistant Examiner—John C. Fox
Attorney, Agent, or Firm—Larry R. Cassett; Roger M. Rathbun

[57] ABSTRACT

A medical gas adapter useable for connecting a gas tubing or other end use device to a gas service outlet to supply the gas for its end use. The adapter has a fixed adapter assembly including an elongated nose that fits within the gas service outlet to activate a valve for releasing gas to the adapter. The fixed adapter assembly also includes a connector means at its other end for connection to the end use device. A release knob is rotatably affixed to the fixed adapter assembly and can be rotated between a first position where a locking mechanism retains the adapter held within the service outlet and a second position where the adapter is released from the service outlet. The release knob is spring biased to return to its first position in the preferred embodiment by a pair of molded leaf springs integrally molded with the release knob for inexpensive manufacture and assembly. The leaf springs are distorted by a pair of disc studs that are fixed to the fixed adapter assembly but cause the distortion in the leaf springs as the leaf springs are rotated about the disc studs. As such, therefore, in its second position, the spring bias causes the release knob to snap back to its first position when released by the user.

9 Claims, 3 Drawing Sheets

MEDICAL GAS ADAPTER WITH MOLDED SPRING BIAS

BACKGROUND OF THE INVENTION

This invention relates to medical gas service outlets and adapters that are used to receive gas from such outlets for delivery of that gas to some end use.

Such outlets are quite common in hospital rooms where gas services such as oxygen, air, nitrous oxide as well as vacuum service can be provided. The user can conveniently plug in the various equipment that utilizes the particular service with a specially designed, keyed adapter that generally is connected to medical tubing for delivery to its end use device.

A typical example of such outlets can be seen in U.S. Pat. No. 3,563,267, C. S. Thompson and 4,190,075, J. P. Kayser. In particular, an adapter is shown and described in U.S. Pat. No. 2,905,487 of H. Schifter. In the Schifter patent, the adapter is inserted into the service outlet until it reaches its desired position where it is engaged and held in place by a hair pin shaped wire spring that straddles a cylindrical projection on the adapter and fits within flats cut into the projection. To remove the adapter, the cylindrical projection is rotated such that the flats are twisted away from the retaining wire spring and the wire spring legs are spread such that the spring legs are no longer seated within the flats. The adapter can thus be removed from the service outlet. Such adapters normally provide that the cylindrical projection is spring biased so that it snaps back to its original position once removal has been effected.

One difficulty with such adapters is in their manufacture and assembly. One type currently available, is similar to that shown in U.S. Pat. No. 2,905,487 and requires a number of components that must be individually assembled during manufacture. Thos components include a coiled wire spring that is fitted quite meticulously into the adapter during assembly and which creates the spring bias to return the cylindrical Projector to its original position when released by the user. Not only is the individual spring relatively expensive but it requires preloading by an assembler during assembly of an adapter to align and insert the spring. The overall schifter type of adapter also requires a plurality of parts that are costly in terms of both material and labor. Obviously, any cost in a product that is mass produced is not desirable if an alternative can be utilized having fewer parts and less tedious assembly.

SUMMARY OF THE INVENTION

In accordance with the present invention, an adapter for use with a medical gas service outlet is provided having fewer parts and increased ease of assembly in order to be more readily manufacturable at a lower cost.

The adapter is useable in place of present adapters without modification of the normal service outlet, thus can immediately be employed for new uses and/or retrofitted to existing uses without modification of service outlets. The adapter has fewer parts, thereby reducing material costs and can be more easily assembled, both in terms of parts as well as tedious assembly steps.

In essence, the adapter comprises an adapter assembly that is press fitted together and which has a connector at one end for connection to an end use, including, of course, a hose leading to some gas or vacuum utilization device. At the other end of the adapter assembly is an elongated nose that fits dimensionally within the standard medical gas service outlet and which, when inserted, opens up various valving means within the service outlet. A passageway for the gas obviously is provided from the end of the elongated nos positioned within the service outlet through the adapter to its connector, thus gas may move from the service outlet through the adapter upon its insertion into the service outlet.

A release knob is affixed to the adapter assembly and rotates with respect to the adapter assembly between a first Position and a second position and has a cylindrical extension that surrounds the elongated nose and which enters the gas service outlet. In the first position, a pair of recesses or flats formed in the cylindrical extension of the release knob receive the normal hairpin shaped spring located within the service outlet and which retains the adapter in its engaged position within the service outlet.

The release knob can be rotated manually by a user to its second position, thereby radially moving the flats to spread the legs of the hairpin shaped spring out of engagement with the flats so that the adapter may be removed therefrom. When the release knob is released by the user, a spring bias causes the release knob to snap back to its first position, ready for insertion and retention within a service outlet.

The spring bias or springing mechanism functions similar to the standard adapter presently on the market, however, the actual spring biasing of the release knob to its first, or lockable position, is accomplished through novel means.

The release knob, color coded to its service outlet, is a molded unitary plastic part and includes not only the cylindrical extension but also includes, in the preferred embodiment, a pair of leaf springs injected molded into the release knob as an integral part thereof. Those leaf springs provide the spring bias that returns the release knob to its original, or first, position when released by a user.

Accordingly, the expense of a separate coil spring is reduced as is the difficulty of assembly and preloading a coil spring by a hand assembler.

Instead, the two integral leaf springs interact with a pair of keying disc studs of a particular shape that are positioned so as to be adjacent the leaf springs. As the release knob is rotated from its first to its second position, the leaf springs move and are distorted by the fixed keying disc studs. Such distortion creates a spring bias that returns the release knob to its first position when released by the user.

Thus, the overall adapter is more easily assembled. The tedious alignment and preloading of a coil spring is unnecessary and the number of actual parts reduced, therefore, manufacturing costs are also reduced.

DESCRIPTION OF THE PREFERRED EMBODIMENT

Figure 1:
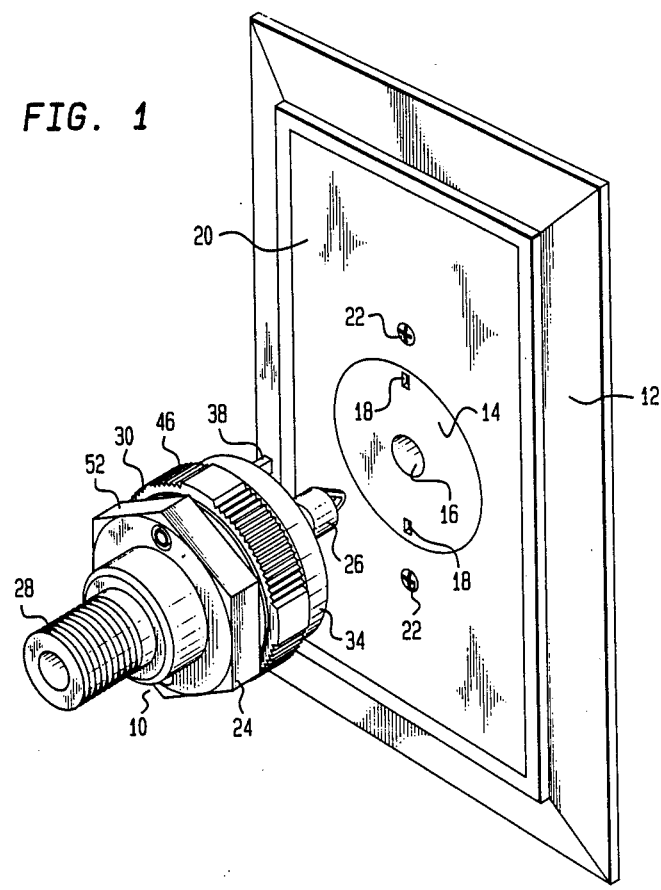
FIG. 1 is a perspective view of a medical gas adapter constructed in accordance with the present invention shown in position for insertion into a gas service outlet.

Referring now to FIG. 1, there is shown a perspective view of a medical gas adapter 10 in position for insertion into a gas outlet 12. Basically, gas outlet 12 is conventional and comprises an outlet face 14 which is normally color coded in accordance with the particular gas being used, or vacuum, and has a center aperture 16 of predetermined diameter and though which the medical service is provided. A pair of keying cavities 18 are found in the outlet face 14 and, as will be explained, are used to insure that the proper medical gas adapter 10 is being used with that particular gas outlet 12.

A faceplate 20 covers the gas outlet 12 and may be secured thereto by conventional means such as screws 22.

Taking now, the medical gas adapter 10 shown in FIG. 1, there is shown an adapter assembly 24 having an elongated nose 26 dimensioned such as to fit within center aperture 16 of the gas outlet 12 for receiving the gas therefrom. The elongated nose seals within gas outlet 12 by means of an O-ring, not shown to provide an unobstructed flow of gas. As referred to in the specification, for brevity, the service will be referred to as delivery of a gas, it being understood that one of the common services to which the present invention can be utilized is a vacuum source.

At the other end of the adapter assembly 24 is a connector 28 for use in connection to an end use device where the medical gas is actively employed. Typically, and as referred to herein, the end use device includes a flexible hose that may be connected to connector 28 for supplying that service. Obviously, the connector 28 shown is a standard threaded connection, however, other types of connections can be used.

A release knob 30 is affixed to the adapter assembly 24 and rotates with respect thereto as will be later explained.

Figure 2:
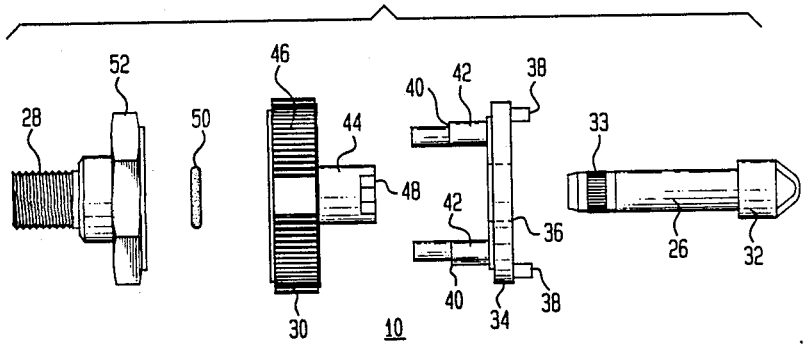
FIG. 2 is an exploded view showing the adapter of FIG. 1 broken down into its component parts.

Taking FIG. 2 in addition to FIG. 1, the detailed parts of the medical gas adapter 10 can be described and the assembly outlined. As shown, the elongated nose 26 of adapter assembly 24 extends outwardly for insertion into the gas outlet 12 and has an enlarged diameter hub 32 at its end to obtain a gas-tight fit sealed within an 0-ring within gas outlet 12. At the other end of elongated nose 26, a knurled section 33 is formed. Elongated nose 26 is preferably made of stainless steel. A keying disc 34 is provided and has an opening 36 though which the elongated nose 26 passes. Keying disc 34 has a plurality of keying lugs 38 and which interfit with the corresponding keying cavities 18 in the outlet face 14. By selecting standard positions for the keying lugs 38 and keying cavities 18, it can be assured that only specific medical gas adapters can be operatively used with certain gas outlets; thus a user cannot inadvertently plug, for example, a nitrous oxide adapter into an oxygen outlet. Keying disc 34 is preferably a zinc die casting and has at least one keying disc stud 40 depending outwardly from keying disc 34 toward the release knob 30. In the preferred embodiment, a pair of keying disc studs 40 are employed since the use of two disc studs 40 and springs provide two opposite forces that are equally distributed and certain friction forces are reduced. As will later become apparent, a portion of the keying disc studs 40 adjacent keying disc 34 is formed into a particular shape, preferably half round studs 42.

Release knob 30 is a unitary molded plastic of a material having low 'creep' characteristics under repeated load application, high toughness, inherent and added lubricity, high strength and adequate stiffness for purposes that will become apparent. One suitable material for release knob 30 is a nylon type material identified as Zytel 70G-13L (13% glass fill, lubricated) available commercially from E.I. DuPont Company. Release knob 30 has a cylindrical extension 44 that surrounds and extends along elongated nose 26 when the medical gas adapter 10 is assembled. Ridges 46 are formed in the outer periphery of release knob 30 for easy grip by a user.

At the extended end of cylindrical extension 44, a pair of flats 48 are formed and which are molded into the cylindrical extension 44 in the shape of cord sections and are formed opposite each other, or about 180° apart.

An O-ring 50 is provided and which, when assembled, fits over the elongated nose 26 to form a gas tight seal there against.

The connector 28 includes a hex flange 52 adaptable for tightening the same for connection to an end use device.

In assembly, therefore, taking FIG. 2, the medical gas adapter 10 is pieced together such that the elongated nose 26 passes through the keying disc 34, release knob 30, O-ring 50 and is press fitted into connection 28. In the assembly thereof, the keying disc studs 40 pass through the hex flange 52 of connection 28 and are secured thereto by spin riveting. Of particular importance, however, in assembly of FIG. 2 parts, the half round studs 42 are positioned within release knob 30, the purpose of which will be explained.

Figure 3:
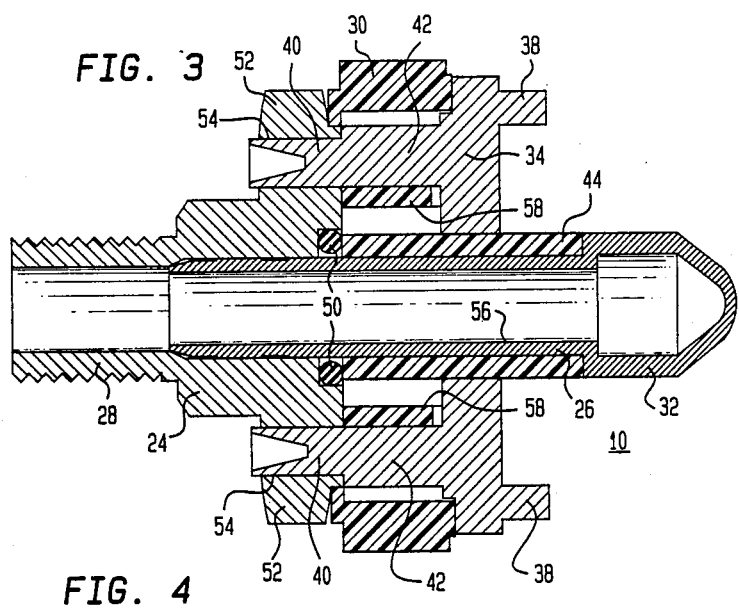
FIG. 3 is a cross-sectional view of the medical gas adapter of the subject invention.

In FIG. 3, therefore, there is shown a side cross-sectional view of the medical gas adapter 10 in its assembled form.

As shown in FIG. 3, the fixed adapter assembly 24 comprise those parts of the medical gas adapter 10 that are fixed with respect to each other and do not move during the securing and releasing of the medical gas adapter 10 in a gas service outlet.

In particular, those parts include the elongated nose 26, the keying disc 34 and connector 28. Such parts are firmly affixed together by the elongated nose 26 force fitted into connector 28 while keying disc 34 is affixed to connector 28 by keying disc studs 40 that pass through openings 54 in hex flange 52 and secured thereto.

As may also be noted when the fixed adapter assembly 24 is assembled, gas can readily pass therethrough by entering the elongated nose 26 from the gas outlet and thereupon pass through the gas passageway 56 that continues out the connector 28 to the end use device.

As also may be seen in FIG. 3, the release knob 30 is sandwiched in between the hex flange 52 of connector 28 and the keying disc 34. Release knob 30 can be rotated with respect to the fixed adapter assembly 24 as will be explained, for moving between a first position where the medical gas adapter 10 is secured within a gas outlet and a second position where the medical gas adapter 10 is released from the gas service outlet.

The release knob 30 is spring biased toward its first position by means of at least one leaf spring 58, however, two leaf springs 58 are shown in FIG. 3 and which is the preferred embodiment. The use of two leaf springs 58 provide balance to the bias forces. Such leaf springs 58 are molded integral within the release knob 30 to assist in the cost-savings of material and assembly time and, specifically, to benefit from the repeatability of the injection molding process.

Figure 4:
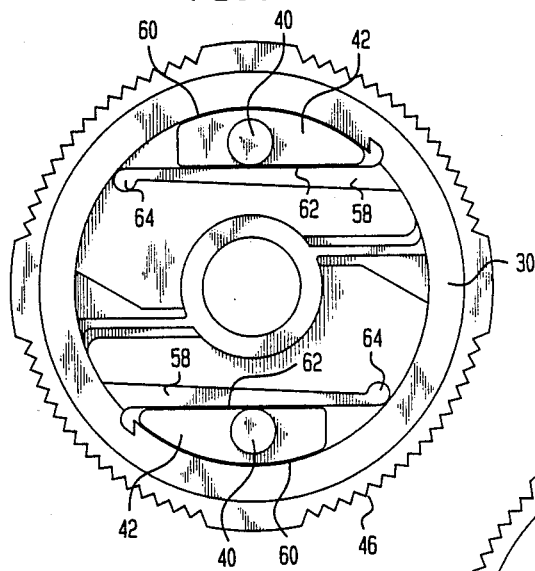
FIG. 4 is an end view with certain parts removed showing the operative features of the medical gas adapter.
Figure 5:
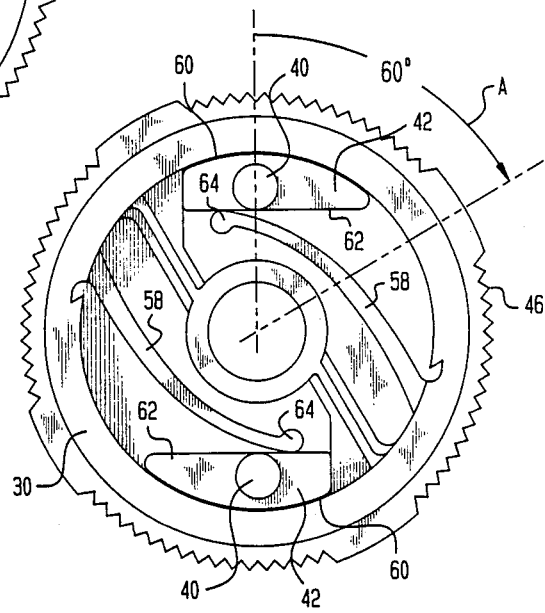
FIG. 5 is an end view as in FIG. 4 showing the spring bias means of the present invention.

Turning new to FIGS. 4 and 5, there is shown a rear view of the spring bias means illustrating the release knob 30 with the connector 28 removed. The half-round studs 42 that depend from keying disc 34 are shown as they pass through release knob 30. The configuration of the half round studs 42, in the preferred embodiment, have a circular outer edge 60 generally conforming to and having a radius slightly less than the radius of the inner surface of the release knob 30. The inner surface 62 of half round studs 42 is relatively planar and at a right angle to a radius emanating from the center of the circular release knob 30. In the preferred embodiment, therefore, the half round studs 42 are opposite each other, 180° apart such that their planar inner surfaces 62 are in parallel planes to each other.

The leaf springs 58 are, as stated, molded integral to the internal surface of release knob 30 as chords and depend inwardly with free ends 64. The outer surface is also generally planar and in the same plane as the inner surface 62 of half round studs 42, that is, the outer surfaces of the two leaf springs 58 that bear upon the half round studs 42 are also in planes parallel to each other and aligned with the parallel Planes of the planar inner surfaces 62 of the half round studs 42. Also, leaf springs 58 are preferably tapered toward the free ends 64.

Turning specifically to FIG. 5, there is shown the same view as FIG. 4, however the release knob 30 has been rotated from its first position ready for insertion into an outlet depicted in FIG. 4 to its second position of approximately 60° in the direction of the arrow A for release from an outlet. In its second position, since the half round studs 42 do not rotate, the release knob 30 appears radially displaced with respect to the FIG. 4 or first position. The planar inner surfaces 62 of half round studs 42 are wedged against the free ends 64 of leaf springs 58, distorting the leaf springs 58 inwardly. Due to the taper of leaf spring 58, the leaf springs 58 undergo approximately constant stress along their length as they are distorted.

That distortion creates a spring bias urging the release knob 30 back towards its first position, and thus, when released by a user, the release knob 30 will quickly snap back to its first position of FIG. 4 to relieve forces created by the distortion of leaf springs 58. It is important to note that the rotation to create the spring bias is limited to the extent that the ends of leaf springs 58 do not move along the planar inner surfaces 62 of half round studs 42 beyond a radius line drawn between the center of rotation or pivot point of leaf springs 58 and meeting the planar inner surfaces 62 at a right angle. If the rotation to create the spring bias passes, to any extent, that point, the leaf springs 58 may become wedged against the planar inner surface 62 and the spring bias effect lost.

Figure 6:
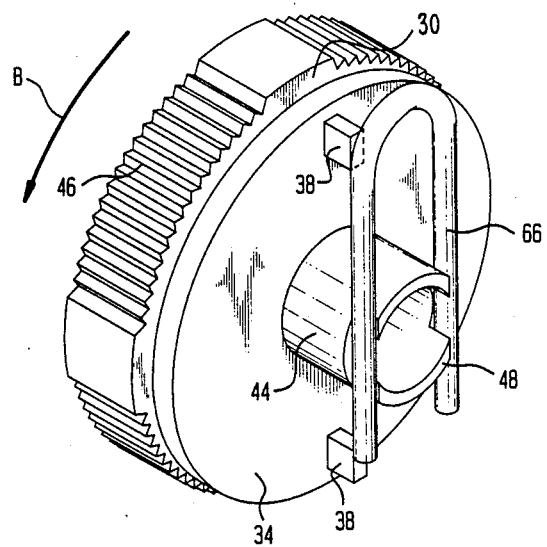
FIG. 6 is a perspective view showing the details of the mechanism that holds the medical gas adapter into a gas service outlet with the release knob in its position for insertion into the gas service outlet.
Figure 7:
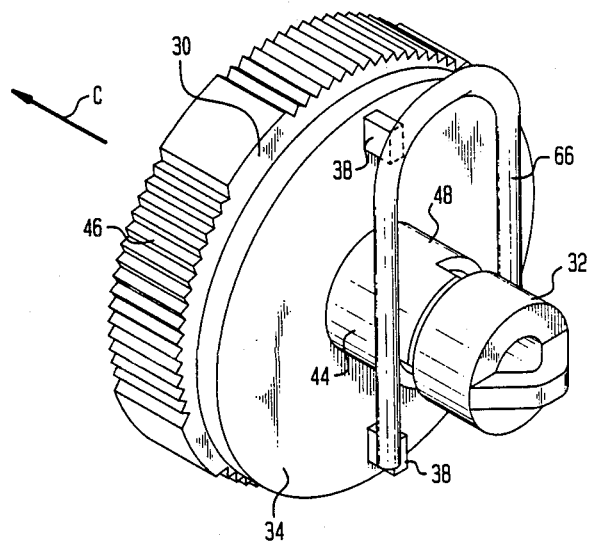
FIG. 7 is a perspective view of the details of FIG. 6 showing the medical gas adapter release knob in the fully rotated position for release from the gas service outlet.

The effect of rotating the release knob 30 between its first and second positions is illustrated in FIGS. 6 and 7 where the release knob 30 is in its first position for insertion into a service outlet in FIG. 6 and its second position for release from a service outlet in FIG. 7. In FIG. 6, the legs of hairpin shaped spring 66 rest within the flats 48 formed in cylindrical extension 44 of the release knob 30. At this position, the hairpin shaped spring 66 can be fixed within a gas outlet and the medical gas adapter 10 is fixed in its position inserted in the outlet since the spring 66 prevents the enlarged diameter hub 32 (see FIG. 3) from being removed past spring 66. Thus, in the first position of release knob 32, the medical gas adapter 10 is fixed in operative position and gas is being provided to the end use device.

To release the medical gas adapter 10 from the gas outlet, the release knob 30 is manually rotated by a user as shown in the direction of the arrow B of FIG. 6 and reaches its second position as depicted in FIG. 7. At this point, the spring 66 is spread out of the flats 48 and the distance between the springs 66 is the same as the diameter of enlarged diameter hub 32 of the elongated nose 26 and, thus, the medical gas adapter 10 may be removed from the gas outlet in the direction of Arrow C. As explained, once removed, the user need merely let go of the release knob 30 for it to snap back to its first position, ready again for insertion into a gas outlet.

By this means, the medical gas outlet 10 has been constructed as to require a reduced number of parts over prior art adapters and its spring bias is provided without preloading or tedious positioning of a coil spring. In essence, the spring bias is molded into the release knob 30, resulting in considerably cost savings in materials and assembly.

We claim:

1. A medical gas adapter for releasable connection to a gas service outlet for use in delivering a gas from the gas service outlet to an end use device, said adapter comprising:

a fixed adapter assembly having an elongated nose for insertion into the gas service outlet and a connector for external connection to an end use device, said fixed adapter assembly having a gas passageway therethrough;

a release knob rotatably affixed to said fixed adapter assembly and having a cylindrical extension surrounding and extending along said nose for releasably securing said medical gas adapter within the gas service outlet, said release knob being rotatable between a first position wherein said adapter is fixed within the service outlet and a second position wherein said adapter is released from the service outlet;

spring bias means adapted to bias said release knob to return to its first position; said spring means comprising at least one stud means fixed with respect to said fixed adapter assembly and extending adjacent said release knob;

and at least one leaf spring integrally molded into said release knob, said at least one leaf spring interfitted against said at least one stud means such that said leaf spring is distorted by said stud means when said release knob is rotated to its second position, said distorted leaf spring thereby biasing said release knob to return to its first position.

2. A medical gas adapter as defined in claim 1 wherein said fixed adapter assembly includes a keying disc affixed thereto and said at least one stud means comprises at least one keying disc stud cast integrally with said keying disc.

3. A medical gas adapter as defined in claim 2 wherein said at least one leaf spring comprises two oppositely disposed leaf springs and said at least one keying disc stud comprises two keying disc studs.

4. A medical gas adapter as defined in claim 3 wherein said keying disc studs each have parallel planar surfaces spaced about 180 degrees apart and are interfitted against planar parallel surfaces formed in said leaf springs.

5. A medical gas adapter as defined in claim 4 wherein said leaf springs are tapered toward said free ends.

6. A medical gas adapter as defined in claim 4 wherein said free ends of said leaf springs have parallel planar surfaces and are interfitted adjacent parallel planar surfaces formed in said respective keying disc studs.

7. A medical gas adapter as defined in claim 4 wherein said opening in said release knob is circular and said leaf springs each form a chord of said circular opening.

8. A medical gas adapter as defined in claim 2 wherein said release knob is comprised of a glass filled polyamide (nylon) material.

9. A medical gas adapter for releasable connection to a gas service outlet for use in delivering a gas from the gas service outlet to an end use device, said adapter comprising:

a fixed adapter assembly having an elongated nose for insertion into the gas service outlet and means for external connection to an end use device, said fixed adapter assembly having a gas passageway therethrough;

a release knob rotatably affixed to said fixed adapter assembly and having a cylindrical extension surrounding and extending along said elongated nose for releasably securing said medical gas adapter within the gas service outlet, said release knob having an opening and being rotatable between a first position wherein said medical gas adapter is fixed within the service outlet and a second position wherein said medical adapter is released from the service outlet;

a pair of keying disc studs fixed to said fixed adapter assembly and extending therefrom through said opening in said release knob, a pair of leaf springs integrally molded into said release knob depending inwardly into said opening and having free ends ending within said opening, said leaf springs having their free ends interfitted adjacent to said keying disc studs such that the free ends of said leaf springs are distorted by said keying disc stud when said release knob is rotated from said first position to said second position, said distorted leaf springs thereby biasing said release knob to return to said first position;

* * * * *